United States Patent
Lee et al.

(10) Patent No.: US 9,873,721 B2
(45) Date of Patent: Jan. 23, 2018

(54) FLUORESCENT FUSION PROTEIN

(71) Applicant: NATIONAL YANG-MING UNIVERSITY, Taipei (TW)

(72) Inventors: Yi-Jang Lee, Taipei (TW); Bo-Sheng Wang, Taipei (TW); Liang-Ting Lin, Taipei (TW); C.Allen Chang, Taipei (TW); Jyh-Cheng Chen, Taipei (TW)

(73) Assignee: National Yang-Ming University, Taipei (TW)

( * ) Notice: Subject to any disclaimer, the term of this patent is extended or adjusted under 35 U.S.C. 154(b) by 324 days.

(21) Appl. No.: 14/543,238

(22) Filed: Nov. 17, 2014

(65) Prior Publication Data

US 2015/0361145 A1    Dec. 17, 2015

(30) Foreign Application Priority Data

Jun. 13, 2014  (TW) ............... 103120460 A (51) Int. Cl.
| | |
|---|---|
| *A61K 51/00* | (2006.01) |
| *A61M 36/14* | (2006.01) |
| *C07K 14/435* | (2006.01) |
| *A61K 49/00* | (2006.01) |
| *G01N 33/50* | (2006.01) |
| *C12Q 1/02* | (2006.01) |

(52) U.S. Cl.
CPC .... *C07K 14/43595* (2013.01); *A61K 49/0047* (2013.01); *C12Q 1/02* (2013.01); *G01N 33/5005* (2013.01); *C07K 2319/01* (2013.01); *C07K 2319/60* (2013.01)

(58) Field of Classification Search
CPC ...... A61K 49/00; A61K 49/0047; C12Q 1/02; G01N 33/5005; C07K 2319/01; C07K 14/43595; C07K 2319/60
USPC .... 424/1.11, 1.65, 1.69, 9.1, 9.6; 514/1, 1.1; 530/300; 223/223, 569, 570; 206/223, 206/569, 570
See application file for complete search history.

(56) References Cited

U.S. PATENT DOCUMENTS 7,687,614 B2 *  3/2010  Campbell ........ C07K 14/43595
                                                    435/106

OTHER PUBLICATIONS

Lin et al., "mPlum-IFP 1.4 fluorescent fusion protein may display Förster resonance energy transfer associated properties that can be used for near-infrared based reporter gene imaging", Journal of Biomedical Optics, Dec. 2013, pp. 126013-1-126013-9, No. 18(12).

* cited by examiner

*Primary Examiner* — D L Jones
(74) *Attorney, Agent, or Firm* — Muncy, Geissler, Olds & Lowe, P.C.

(57) ABSTRACT

A fluorescent fusion protein is provided. The fluorescent fusion protein of the invention comprises a first fluorescent protein with first emission wavelength, a second fluorescent protein with second excitation wavelength and second emission wavelength, and a linker peptide linking the first fusion protein and the second fusion protein, wherein the first emission wavelength overlaps the second excitation wavelength so that the second fluorescent protein exhibits the second emission wavelength after receiving energy. The fluorescent fusion protein of the invention exhibits a stronger fluorescence in the absence of bilivirdin (BV).

6 Claims, 14 Drawing Sheets
(6 of 14 Drawing Sheet(s) Filed in Color)

SEQUENCE LISTING

<160> NUMBER OF SEQ ID NOS: 2

<210> SEQ ID NO 1
<211> LENGTH: 8
<212> TYPE: PRT
<213> ORGANISM: Artificial Sequence
<220> FEATURE:
<223> OTHER INFORMATION: linker peptide

<400> SEQUENCE: 1

Arg Gln Leu Glu Lys Leu Ala Thr
1               5

<210> SEQ ID NO 2
<211> LENGTH: 24
<212> TYPE: DNA
<213> ORGANISM: Artificial Sequence
<220> FEATURE:
<223> OTHER INFORMATION: The nucleic acid sequence for linker peptide.
      The nucleic acid sequence synthesized from the laboratory.

<400> SEQUENCE: 2
cgccagctcg agaagcttgc cacc                                          24

FLUORESCENT FUSION PROTEIN

CROSS-REFERENCE TO RELATED APPLICATIONS

This Non-provisional application claims priority under 35 U.S.C. § 119(a) on Patent Application No(s). [103120460] filed in Taiwan, Republic of China [Jun. 13, 2014], the entire contents of which are hereby incorporated by reference.

FIELD OF THE INVENTION

The present invention relates to a novel fluorescent fusion protein, and in particular relates to a fluorescent fusion protein having two different fluorescent proteins.

DESCRIPTION OF THE RELATED ART

The identification and isolation of fluorescent proteins in various organisms, including marine organisms, has provided a valuable tool to molecular biology. The green fluorescent protein (GFP) of the jellyfish *Aequorea victoria*, for example, has become a commonly used reporter molecule for examining various cellular process, including the regulation of gene expression, the localization and interactions of cellular proteins, the pH of intracellular compartments, and the activities of enzymes.

The usefulness of *Aequorea* GFP has led to the identification of numerous other fluorescent proteins in an effort to obtain proteins having different useful fluorescence characteristics. In addition, spectral variants of *Aequorea* GFP have been engineered, thus providing proteins that are excited or fluoresce at different wavelengths, for different periods of time, and under different conditions. The availability of such fluorescent proteins has greatly expanded the studies that the proteins can be used for and, consequently, our understanding of cellular structure and function.

Visibly fluorescent proteins (FPs) from jellyfish and corals have revolutionized many areas of molecular and cell biology, but the use of FPs in intact animals such as mice has been handicapped by poor penetration of excitation light. In vivo optical imaging of deep tissues in animals is most feasible between 650 and 900 nm because such wavelengths minimize the absorbance by hemoglobin, water and lipids as well as light scattering (F. F. Jöbsis, *Science* 198. 1264 (1977); R. Weissleder, V. Ntziachristos, *Nat. Med.* 9, 123 (2003)). Thus, genetically encoded, infrared FPs (IFPs) would be particularly valuable for whole-body imaging in cancer diagnosis and treatment, stem cell biology, gene therapy, and other areas of medical research and treatment (T. Schroeder, *Nature* 453, 345 (2008); R. Weissleder, M. J. Pittet, *Nature* 452, 580 (2008)).

However, excitation and emission maxima of FPs in vivo have not exceeded 598 and 655 nm respectively (D. Shcherbo et al., *Nat. Methods* 4, 741 (2007); M. A. Shkrob et al., *Biochem. J.* 392, 649 (2005); L. Wang, W. C. Jackson, P. A. Steinbach, R. Y. Tsien, *Proc. Natl. Acad. Sci. U.S.A.* 101, 16745 (2004)). Somewhat longer wavelengths (644 nm excitation, 672 nm emission) have been observed in a phytochrome-based FP that incorporates phycocyanobilin (PCB) as the chromophore (A. J. Fischer, J. C. Lagarias, *Proc. Natl. Acad. Sci. U.S.A.* 101, 17334 (2004)).

The disadvantages of current FPs includes that the signals emitted from FPs in deep tissue of animals is too weak for detection although the long-wavelength FPs have a high-penetration transmission. In addition, it is not easy to detect short-wavelength FPs in animal because its penetration rate is too low. The short-wavelength FPs is only used in single-cell level.

Therefore, a novel fluorescent protein with high penetration is needed to be useful for imaging and easy for observation in vivo.

SUMMARY OF THE INVENTION

In view of the above-mentioned problems, the present invention provides a fluorescent fusion protein having a high excitation wavelength. Compared with traditional infrared fluorescent protein, the fluorescent fusion protein provides a higher infrared light. The expression of fluorescent fusion protein of the invention could be detected in mammalian cells and in tumors for in vivo imaging of deep tissues or lesions.

The fluorescent fusion protein of the invention comprises (1) a first fluorescent protein with a first emission wavelength, (2) a linker peptide linking the C-terminal of the first fusion protein, wherein the linker peptide has a sequence of RQLEKLAT (SEQ ID: NO.:1), and (3) a second fluorescent protein linking the C-terminal of the linker peptide, wherein the second fluorescent protein has a second excitation wavelength and a second emission wavelength, and the first emission wavelength overlaps the second excitation wavelength so that the second fluorescent protein exhibits the second emission wavelength after receiving energy.

In one embodiment, the first fluorescent protein is selected from a group consisting of mPlum, mGrape2, mRaspberry, mGrape1 and mCherry.

In one embodiment, the first emission wavelength is between 600 nm and 690 nm.

In one embodiment, the second fluorescent protein is selected from a group consisting of IFP, mPlum, mGrape2, mRaspberry, and mGrape1.

In one embodiment, the second excitation wavelength is between 600 nm and 690 nm.

In one embodiment, the second emission wavelength is between 620 nm and 708 nm.

The invention also provides a nucleic acid sequence encoding the fluorescent fusion protein of the invention comprising, (1) a nucleic acid sequence encoding a first fluorescent protein, (2) a linker peptide having a nucleic acid sequence of CGC CAG CTC GAG AAG CTT GCC ACC (SEQ ID NO.: 2), and (3) a nucleic acid sequence encoding a second fluorescent protein, wherein the C-terminal of the nucleic acid sequence encoding the first fluorescent protein is linked with the N-terminal of the linker peptide, and the N-terminal of the nucleic acid sequence encoding the second fluorescent protein is linked with the C-terminal of the nucleic acid sequence encoding the linker peptide.

In one embodiment, the first fluorescent protein is selected from a group consisting of mPlum, mGrape2, mRaspberry, mGrape1 and mCherry.

In one embodiment, the second fluorescent protein is selected from a group consisting of IFP, mPlum, mGrape2, mRaspberry, and mGrape1.

The invention further provides a kit, comprising the fluorescent fusion protein of the invention.

The invention further provides a vector, comprising the nucleic acid sequence encoding the fluorescent fusion protein of the invention.

The invention further provides an imaging method, comprising (1) expressing the fluorescent fusion protein of the invention in a living subject in vivo, and (2) observing the subject by an imaging device.

In one embodiment, the living subject comprises a cell, plant or animal.

A detailed description is given in the following embodiments with reference to the accompanying drawings.

BRIEF DESCRIPTION OF DRAWINGS

The patent or application file contains at least one drawing executed in color. Copies of this patent or patent application publication with color drawing(s) will be provided by the Office upon request and payment of the necessary fee.

The present invention can be more fully understood by reading the subsequent detailed description and examples with references made to the accompanying drawings, wherein.

DETAILED DESCRIPTION OF INVENTION

The following description is of the best-contemplated mode of carrying out the invention. This description is made for the purpose of illustrating the general principles of the invention and should not be taken in a limiting sense. The scope of the invention is best determined by reference to the appended claims.

The invention provides a fluorescent fusion protein. The fluorescent fusion protein of the invention comprises (1) a first fluorescent protein with a first emission wavelength, (2) a linker peptide linking the C-terminal of the first fusion protein, wherein the linker peptide has a sequence of RQLE-KLAT (SEQ ID: NO.:1), and (3) a second fluorescent protein linking the C-terminal of the linker peptide, wherein the second fluorescent protein has a second excitation wavelength and a second emission wavelength.

The "fluorescent protein" of the invention refers to any protein which emits fluorescence by electromagnetic radiation. In particular, GFP and its spectral variants, as well as other naturally occurring fluorescent proteins have a propensity to self-associate under physiological conditions. The variants refer to any protein that is different from naturally occurring fluorescent proteins. For example, a naturally occurring GFP can be mutated such as amino acids substitution, to form a GFP variant.

The first fluorescent protein of the invention can be any fluorescent protein, preferably, mPlum, mGrape2, mRaspberry, mGrape1 or mCherry, more preferably, mPlum. It shall be noted that, the first fluorescent protein has a first emission wavelength between 600 nm and 690 nm, preferably, 610 nm and 648 nm, more preferably, 595 nm and 684 nm.

In one embodiment, the first fluorescent protein of the invention is selected form a group consisting of mPlum, mGrape2, mRaspberry, mGrape1 and mCherry.

The second fluorescent protein of the invention can be any fluorescent protein, preferably, IFP, mPlum, mGrape2, mRaspberry or mGrape, more preferably, IFP. It shall be noted that the second fluorescent protein has a second excitation wavelength and a second emission wavelength. The second excitation wavelength is between 600 nm and 690 nm, preferably, 610 nm and 648 nm, more preferably, 595 nm and 684 nm, and the second emission wavelength is between 620 nm and 708 nm, preferably, 630 nm and 710 nm, more preferably, 650 nm and 715 nm.

In one embodiment, the second fluorescent protein of the invention is selected form a group consisting of IFP, mPlum, mGrape2, mRaspberry and mGrape.

In one preferred embodiment, the first fluorescent protein is mPlum and the second fluorescent protein is IFP 1.4.

It shall be noted that the emission wavelength of the first fluorescent protein (first emission wavelength) overlaps the excitation wavelength of the second fluorescent protein (second excitation wavelength), such as at least 30%, 40%, 50%, 60%, 70%, 80%, 90%, 95%, and 99% of overlap. The fluorescent fusion protein therefore can excite the emission light of the second fluorescent protein through fluorescence excitation energy transfer by the emission light of the first fluorescent protein. The emission light of the second fluorescent protein can be useful for imaging of living subjects and observation of deep tissues in vivo, because the emission light of the second fluorescent protein has a wavelength exceeding 700 nm.

The first fluorescent protein and the second fluorescent protein can be linked by at least one linker peptide. The linker peptide of the invention can be a short-chain peptide. The linker peptide includes at least one amino acid, preferably 2 to 15 amino acids, more preferably, 5 to 10 amino acids, most preferably 8 amino acids. In a specific embodiment, the linker peptide preferably has a sequence of SEQ ID NO: 1.

The invention further provides a nucleic acid sequence encoding the fluorescent fusion protein of the invention, a vector containing the nucleic acids, and a host containing the nucleic acids or vector. The invention provides a recombinant nucleotide sequence, comprising at least one nucleic acid sequence encoding the fluorescent protein of the invention. The recombinant nucleotide sequence can be included in the vector, and the vector can be an expression vector.

The vector of the invention comprises the nucleic acid sequences of fluorescent fusion protein and the linker peptide. In one embodiment, the linker peptide preferably has a sequence of SEQ ID NO: 2.

The vectors of the invention can contain elements required for replication in a prokaryotic (e.g., bacterial) or eukaryotic (e.g., insect, yeast (e.g., Pichia) and/or mammalian) host system or both, as desired. The vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.; Invitrogen Corp., Carlsbad Calif.) or can be constructed by one skilled in the art (see, for example, Meth. Enzymol., Vol. 185, Goeddel, ed. (Academic Press, Inc., 1990); Jolly, Canc. Gene Ther. 1:51-64, 1994; Flotte, J. Bioenerg. Biomemb. 25:37-42, 1993; Kirshenbaum et al., J. Clin. Invest. 92:381-387, 1993).

Expression vectors containing regulatory elements from eukaryotic viruses are typically used, such as SV40 vectors, bovine papaloma virus, and vectors derived from Epstein Bar virus. Other exemplary vectors include pMSG, pAV009/A+, pMT010/A+, pMAMneo-5, bacculovirus pDSVE, and any other vector allowing expression of glycoproteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

Transformation of the host cells with the vector(s) may be performed using any transformation methodology known in the art, the host cells may be transformed as bacteria, mammalian cells, yeasts or intact cells, then purified using standard techniques. (see, e.g., Colley et al., J. Biol. Chem. 264:17619-17622 (1989) and Guide to Protein Purification. Vol. 182, Methods in Enzymology (Deutscher ed., 1990)). Transformation methodologies of Prokaryotic and eukaryotic cell are shown in Morrison, J. Bact., 132:349-351 (1977); Clark-Curtiss & Curtiss, Methods in Enzymology, 101:347-362 (Wu et al., eds, 1983).

The invention further provides a kit comprising the fluorescent fusion protein of the invention. The vector can includes one or more the fluorescent fusion proteins of the invention. The kit of the invention also can includes one or more the nucleic acids sequences encoding the fluorescent fusion protein of the invention which may be the same or different. Additionally, the kit of the invention also includes an instruction for use.

The invention further provides a method for imaging, comprising expressing the fluorescent fusion of the invention in a living subject in vivo, and observing the subject by a imaging device.

The imaging device may be any kinds of fluorescence microscopy such as a confocal or non-confocal fluorescent microscopy.

It shall be noted that fluorescence enhancers are not required in the imaging method of the invention, because of the fluorescent fusion protein of the invention with a high fluorescence intensity and long wavelength emission. The method of the invention thus can be useful for imaging of living subjects in the absence of fluorescence enhancers.

As mentioned above, the fluorescence enhancers are not needed so that experimental errors can be decreased. Moreover, the fusion protein of the invention can be used to image the living subjects and observe the deep tissues, since it can emit long-wavelength fluorescence.

EXAMPLE 1

Preparation and Transfection of Vectors

The pcDNA3-IFP1.4-IRES-GFP construct was kindly provided by Dr. Roger Y. Tsien, University of California, San Diego. The pmPlum vector was purchased from Clontech Laboratories Inc. (Clontech Laboratories Inc., Mountain View, Calif.) and the embedded mPlum gene was amplified from this vector using a polymerase chain reaction (PCR).

The sequence of forward primer was 5'-GACCATGATTACGCCAAGCTT GCATGCCTGCAGGTCGACTC-3'. Three reversal primers containing different lengths of linkers were used, namely 5'-CCCAAGCTTGGCGCCGGTGGAGTG-3' (linker #1), 5'-CCCAAGCTTCTCGAGCTGGCGGCGCCGGTGGAGTGG-3' (linker #2), and 5'-CCCAAGCTTGCCTCCACACTCTCCGAGAGCGGTACAACACTCTCCGAGAGCGGTACAACACTCTCCGAGAGCGGTAAGCTTCTCGAGCCAGCGGCGCCGGTGGAGTGG-3' (linker #3).

The amplified mPlum fragments with different lengths of linkers were then digested with Hind III and separately ligated upstream of the IFP 1.4 DNA sequence in the pcDNA3-IFP1.4-IRES-GFP construct.

This plasmid was subjected to DNA sequencing analysis using a primer that was designed from the cytomegalovirus promoter to demonstrate the anticipated in-frame nucleotide linkage of these two proteins.

SV40 large T-antigen transformed human embryonic kidney 293 cells (293T) were purchased from Bioresource Collection and Research Center in Taiwan (BCRC, Hsinchu, Taiwan). The cells were cultured in Dulbecco's Modified Eagle Medium and supplemented with 10% fetal bovine serum, 200-mM glutamine, 100 U/mL of penicillin, and 100 μg/mL of streptomycin (Invitrogen Inc. Carlsbad, Calif.). The culture was maintained at 37° C. in a humid incubator with 5% $CO_2$ and passaged every two days. For DNA transfection, $1\times10^6$ cells were seeded into a 10 $cm^2$ plate overnight. The established mPlum-IFP 1.4 fusion protein construct or other plasmids were then transfected into the cells according to the manufacturer's instructions (JetPEI™ transfection agent, Polyplus-transfection SA., Illkirch, France).

EXAMPLE 2

Microscopy Observation

Figure 1:
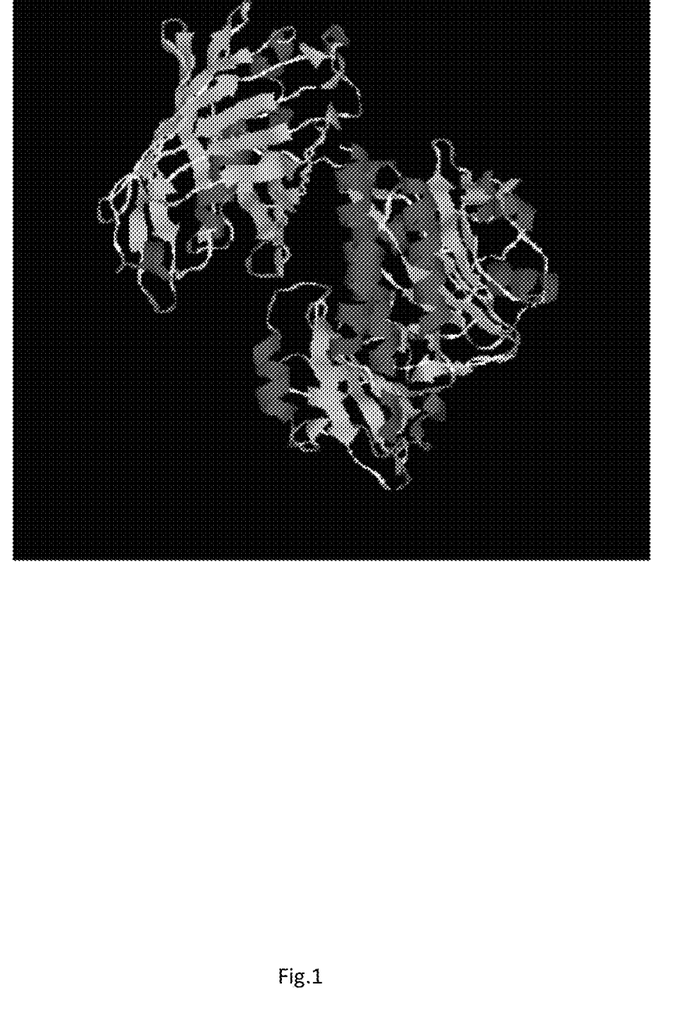
FIG. 1 illustrates a most stable fusion protein structure using the protein structure prediction software I-TASSER. The results show that mPlum and IFP still maintain their original tertiary structure, individually.

For cell imaging, 293T cells that have been transfected with fluorescent protein expressing plasmids were fixed with 4% paraformaldehyde for 10 min on coverslips, rinsed, and mounted using a mounting medium. The cell imaging was visualized and obtained using a laser confocal microscopy containing a chargecoupled device camera (FV1000, Olympus Corporation, Tokyo, Japan). Transfected cells were visualized using the IFP channel of confocal microscopy at an excitation wavelength of 543 or 633 nm. Referring to FIG. 1, the brightness of mPlum-IFP 1.4 fusion protein was stronger than that of IFP 1.4 at 543-nm excitation channel (FIG. 1, D and H), while the brightness of both proteins were comparable at 633-nm excitation channel (FIG. 1, B and F). Individually expressed mPlum and IFP 1.4 were also examined using excitation wavelengths at 543 and 633 nm for comparison with the fusion protein, respectively (FIG. 1, B-D and J-L). Minor IFP signals were captured in mPlum expressing cells by 543- and 633-nm laser excitation, suggesting that mPlum may have partially bleed through in the infrared emission channel (FIG. 1, I and K). Additionally, co-expressed GFP was only detected in cells expressing native IFP 1.4 and mPlum-IFP 1.4 fusion protein, but not in cells expressing mPlum because the pmPlum vector did not contain the GFP expressive cassette (FIG. 1, A, E and I).

Figure 2:
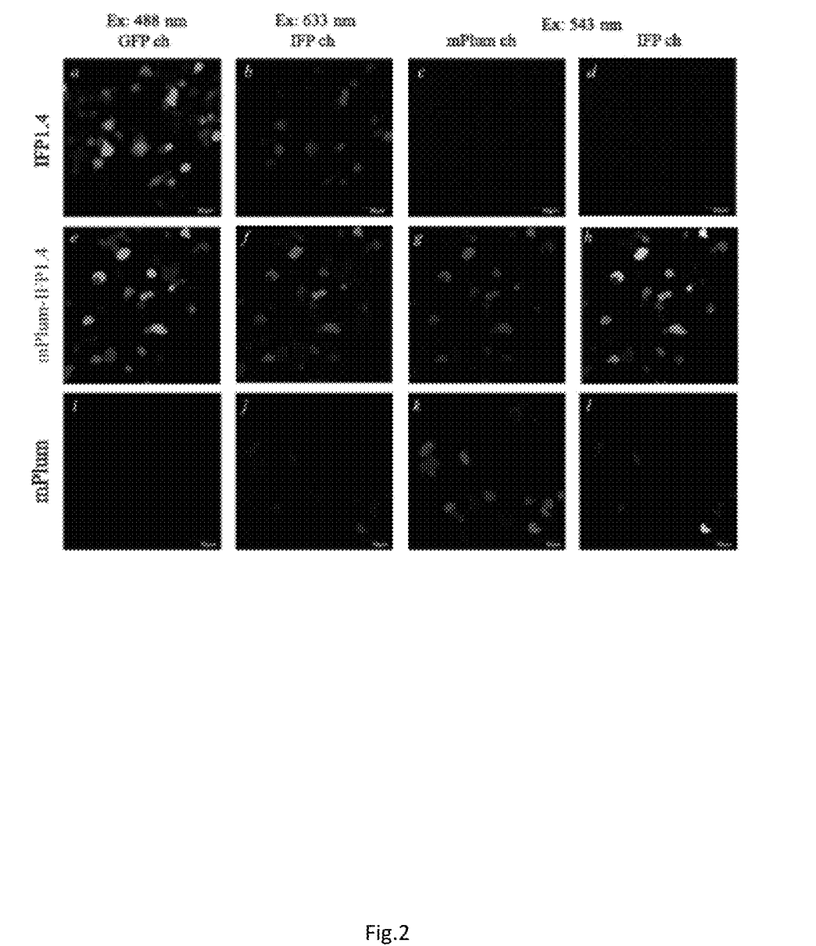
FIG. 2 illustrates the visual images of mPlum, IFP 1.4, and mPlum-IFP 1.4 fusion proteins by a fluorescent microscopy.

Referring to 2, The Western blot analysis also demonstrated that the protein levels of co-expressed GFP in IFP 1.4 and mPlum-IFP 1.4 transfected cells were similar.

Figure 3:
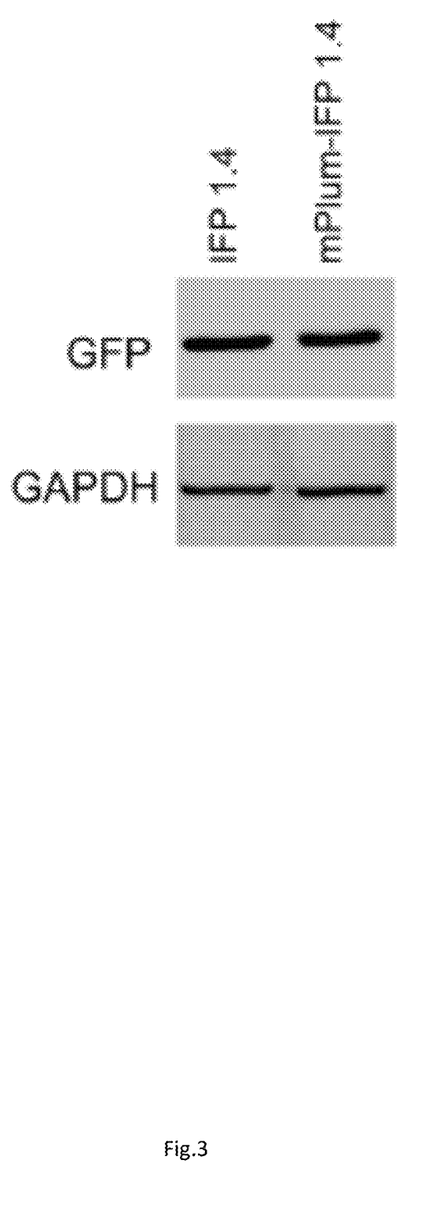
FIG. 3 illustrates the expression level of IFP 1.4 and mPlum-IFP 1.4 fusion proteins in host cells.

Referring to FIG. 3, the fluorescent intensities of the mPlum-IFP 1.4 fusion protein was stronger than that of IFP 1.4 in transfected cells at their optimal excitation wavelength, namely 543 nm for fusion protein and 633 nm for IFP 1.4 protein.

In addition, PT-PCR results indicated that no significant gene expressive difference was detected between IFP 1.4 and mPlum-IFP 1.4. As mentioned above, the brightness of mPlum-IFP 1.4 was stronger than that of IFP 1.4.

EXAMPLE 3

FRET Analysis of mPlum-IFP 1.4 Fusion Protein

For the FRET analysis, images of single 293T cells were acquired at 100× magnification by exciting at 488, 543, and 633 nm to confirm the original expression of GFP, mPlum, and 1FP1.4, respectively, prior to acceptor photobleaching. Subsequently, the 488- and 543-nm channels were shut off and the intensity of the 633-nm channel was switched to 100% in order to photobleach the acceptor (IFP 1.4) in mPlum-IFP 1.4 fusion protein. Twenty-five times of pulsed light excitation was delivered to the slide to achieve the photobleaching. Cell images were then acquired using the 488-, 543-, and 633-nm channels after photobleaching.

The FRET properties were then analyzed using the acceptor photobleaching method, and a Förster critical distance for common resonance energy transfer donor-acceptor pairs in the analytical software that accompanied the Olympus FV1000 microscopy was chosen.

Figure 4:
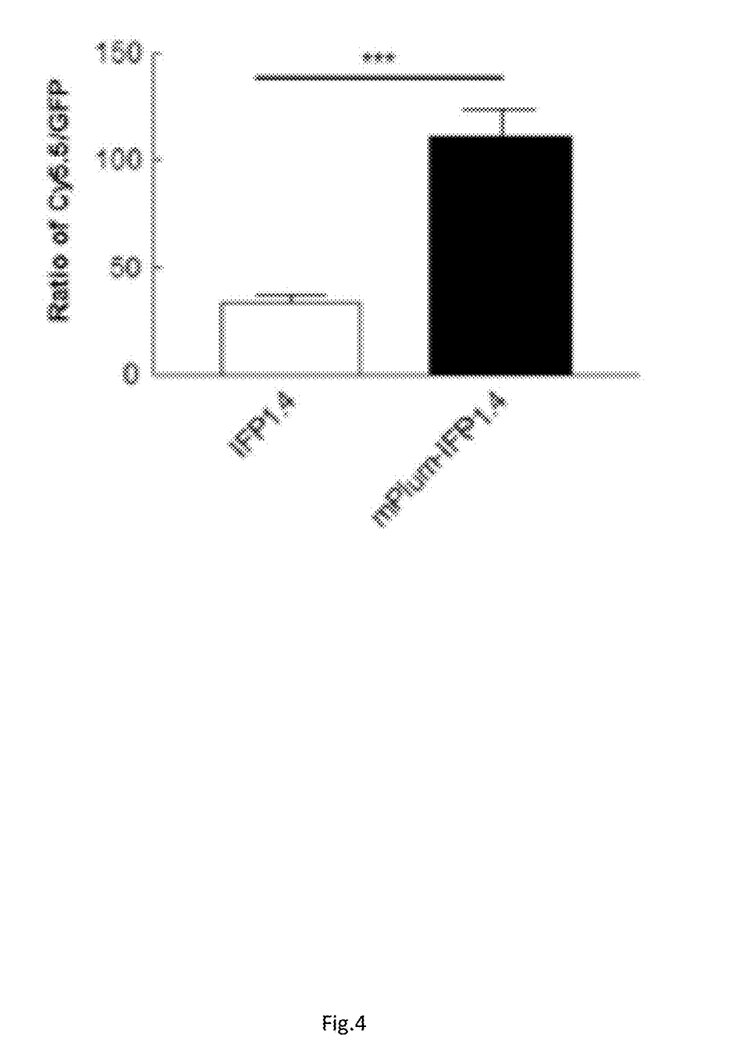
FIG. 4 illustrates the fluorescent light brightness in IFP 1.4 or the mPlum-IFP 1.4 fusion protein.

Referring to FIG. 4a, the excitation and emission spectra of mPlum and IFP 1.4 fluorescent proteins reveal that the emission peak (648 nm) of the mPlum donor closely overlapped the excitation peak (684 nm) of the IFP 1.4 acceptor. Based on this fact, it was investigated that whether the increased fluorescent intensity of the mPlum-IFP 1.4 fusion protein shown above was associated with a FRET phenomenon. First, photobleaching of the IFP 1.4 acceptor showed that the fluorescent intensity of mPlum donor in the fusion protein was increased, and this was an important optical characteristic of the FRET, as shown in FIG. 4b. Increase of mPlum donor fluorescent intensity of the fusion protein after photobleaching was also quantified, and the results were compared to cells co-transfected with mPlum plasmid and IFP 1.4 plasmid, separately (FIG. 4c). According to the mathematic relationship between the FRET efficiency (E) and distance (d) (E is inversely proportional to the sixth power of d), the FRET efficiency and distance in a series of single cells were estimated. The FRET efficiency and donor/acceptor distance of mPlum-IFP 1.4 fusion protein were quantified and compared to individually expressed mPlum and IFP 1.4 in cells (FIGS. 4d and 4e). Therefore, the results indicated that the excitation of mPlum using 543 nm caused emission of IFP fluorescence in mPlum-IFP 1.4 fusion protein (FIG. 1) and was associated with potent FRET mechanism.

EXAMPLE 4

Effects of Bilivirdin (BV) on Fluorescent Intensity of the mPlum-IFP 1.4 Fusion Protein The bilivirdin (BV) was known to increase the fluorescent intensity of IFP 1.4 in vitro and in vivo. Referring to FIG. 5, using the IVIS 50 system, exogenous addition of the BV to IFP 1.4 transfected 293T cells exhibited a dose-dependent increase in photon flux via the Cy5.5 channel (ex/em: 615 to 665 nm/695 to 770 nm).

Figure 5A:
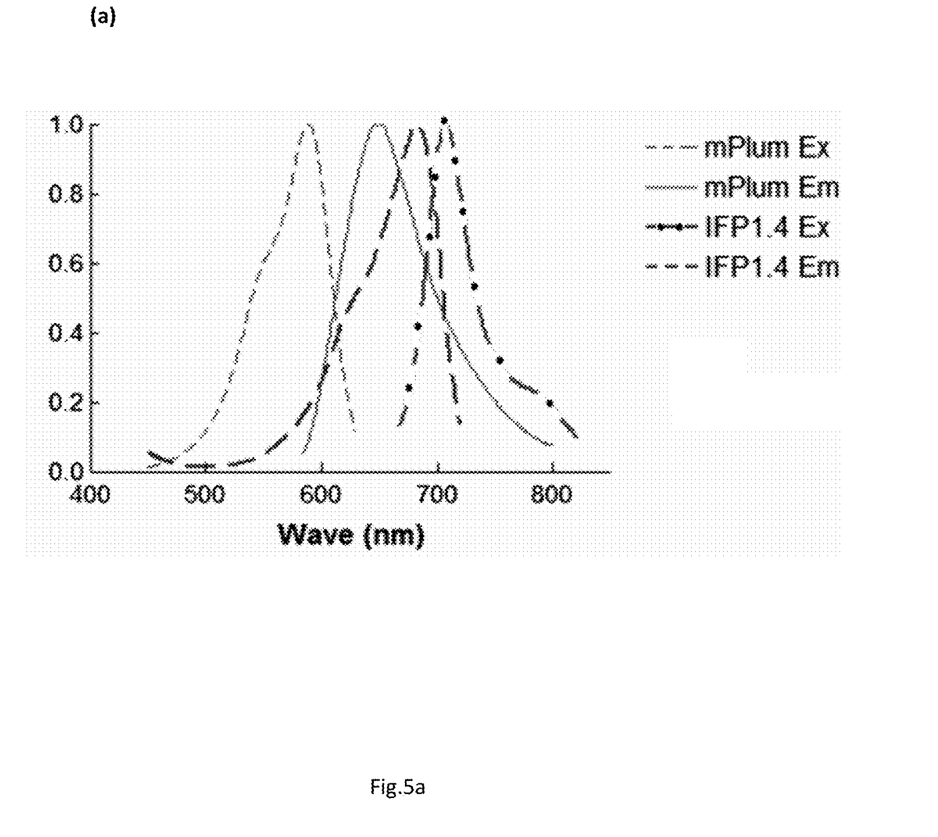
FIG. 5a illustrates the excitation and emission wavelength of mPlum and IFP1.4.
Figure 5B:
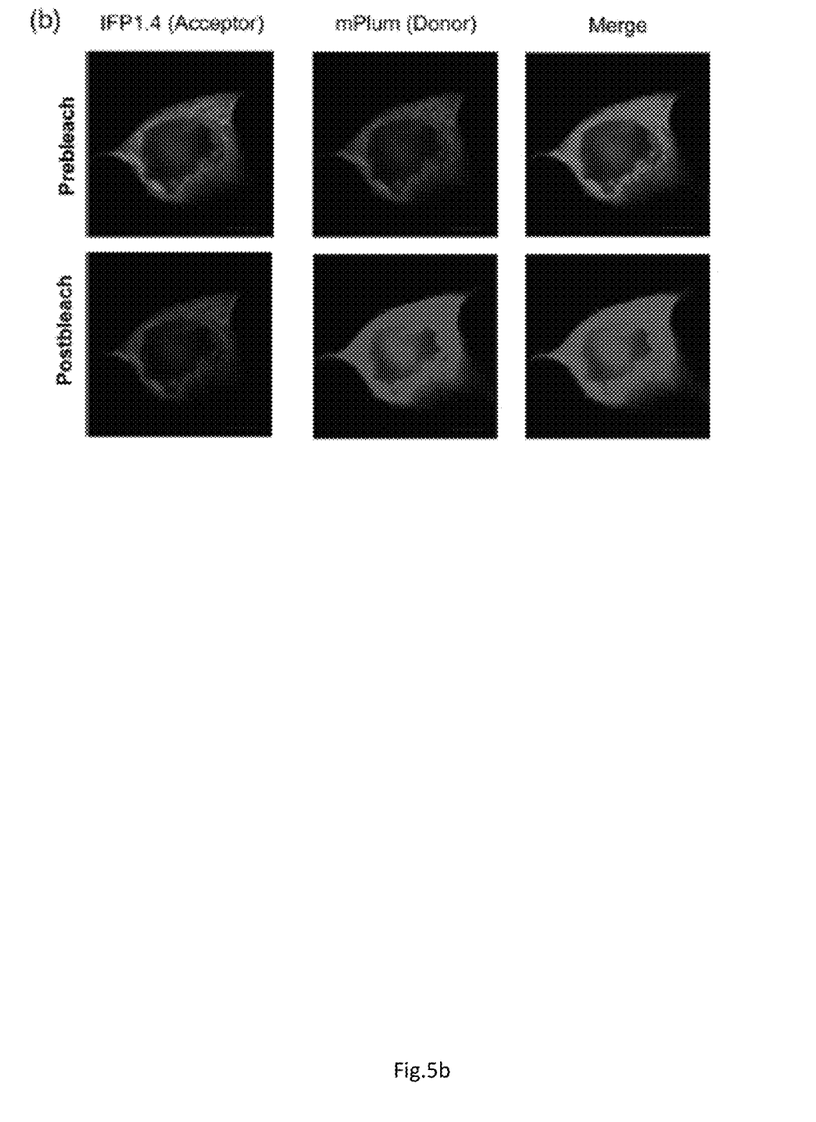
FIG. 5b illustrates the fluorescent light brightness of the mPlum-IFP 1.4 fusion protein before and after photobleaching.

To investigate whether the fluorescent intensity of the mPlum-IFP 1.4 fusion protein was also enhanced by the BV, the IVIS 50 system was again used to detect the photon flux in fusion protein expressing 293T cells in the presence of the BV or solvent only. Interestingly, the results showed that at 580- to 610-nm excitation wavelengths, the mPlum-IFP 1.4 transfected cells exhibited significant fluorescent signals without BV, although the signals were slightly enhanced by adding the BV (FIG. 5b, left side).

On the contrary, the fluorescent signals of native IFP 1.4 could not be detected using the same excitation wavelength range with or without BV. However, the BV significantly enhanced the fluorescent signals of native IFP 1.4 at a 615- to 665-nm excitation range, but, by way of contrast, this did not occur with mPlum-IFP 1.4 fusion protein (FIG. 5b, right side).

Figure 5C:
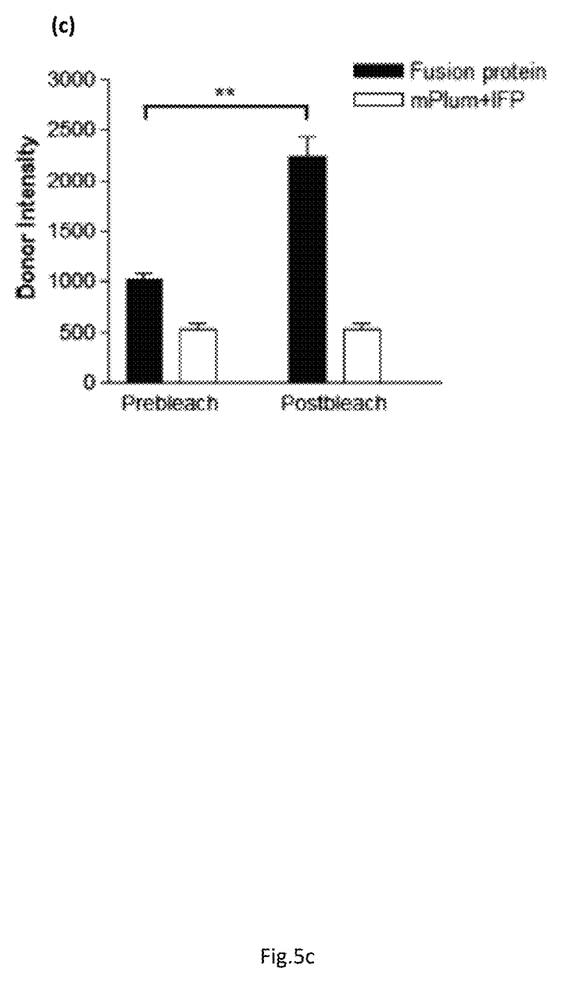
FIG. 5c illustrates the fluorescent light brightness of the mPlum-IFP 1.4 fusion protein and "mPlum+IFP 1.4" protein before and after photobleaching.
Figure 5D:
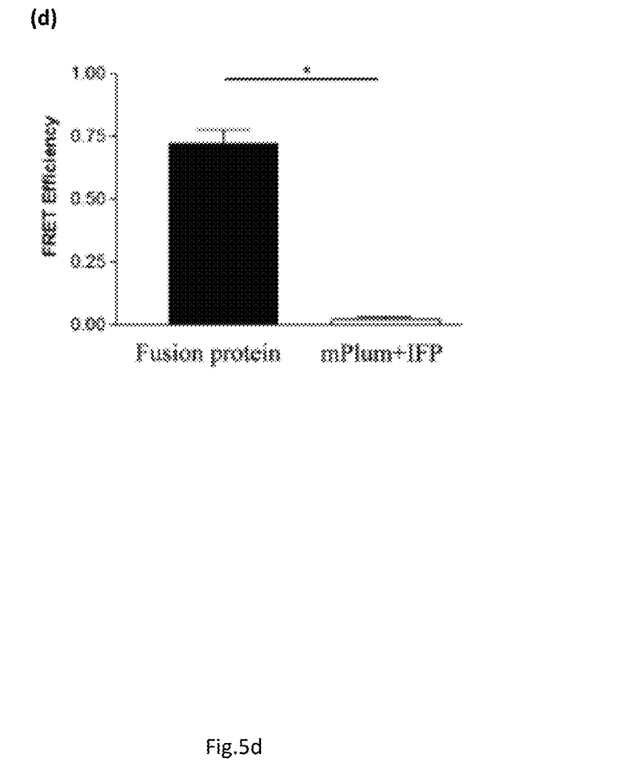
FIG. 5d illustrates FRET efficiency of the mPlum-IFP 1.4 fusion protein and "mPlum+IFP 1.4" protein before and after photobleaching.
Figure 5E:
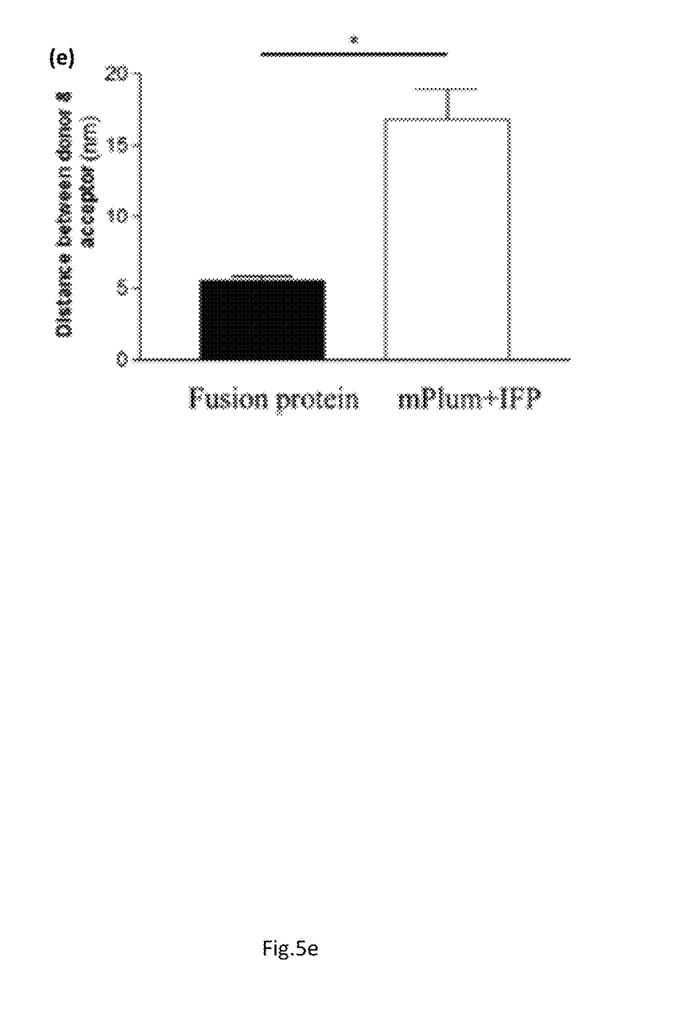
FIG. 5e illustrates donor/acceptor distance of the mPlum-IFP 1.4 fusion protein and "mPlum+IFP 1.4".

Referring to FIG. 5c, quantification of the optical signals further showed that mPlum-IFP 1.4 fusion protein provided an apparent fluorescent signal by 580- to 10-nm excitation, but that was not significantly improved by adding the By. Therefore, exogenous addition of the BV was not required to visualize or enhance fluorescent emission of mPlum-IFP 1.4 fusion protein.

EXAMPLE 5

Noninvasive Imaging of mPlum-IFP 1.4 Fusion Protein Expression in Xenograft Tumors Using Small Animals BALB/cAnN.Cg-Foxn1$^{nu}$/CrlNarl mice were purchased from National Laboratory Animal Center and housed in the animal maintenance room of department of biomedical imaging and radiological sciences, National Yang-Ming University. The animal study was approved (No. 1000616) by Institutional Animal Care and Use Committee (IACUC) of National Yang-Ming University, Taipei, Taiwan.

An in vivo imaging system (IVIS) 50 optical imaging system (PerkinElmer Inc., Walthem, Mass.) was used for the macroscopic detection of the fluorescent intensity of mPlum-IFP 1.4 fusion protein in vivo. Transfected cells after trypsinization were either aliquot in 96-well plates, or subcutaneously implanted into nude mice. Plates were directly placed on the stage of IVIS 50 system, but those implanted animals were imaged 7 days after the inoculation. The BV was dissolved in dimethyl sulfoxide as a 25 mM stock solution. This solution was then added to cells or intravenously injected into animals after dilution.

Figure 6A:
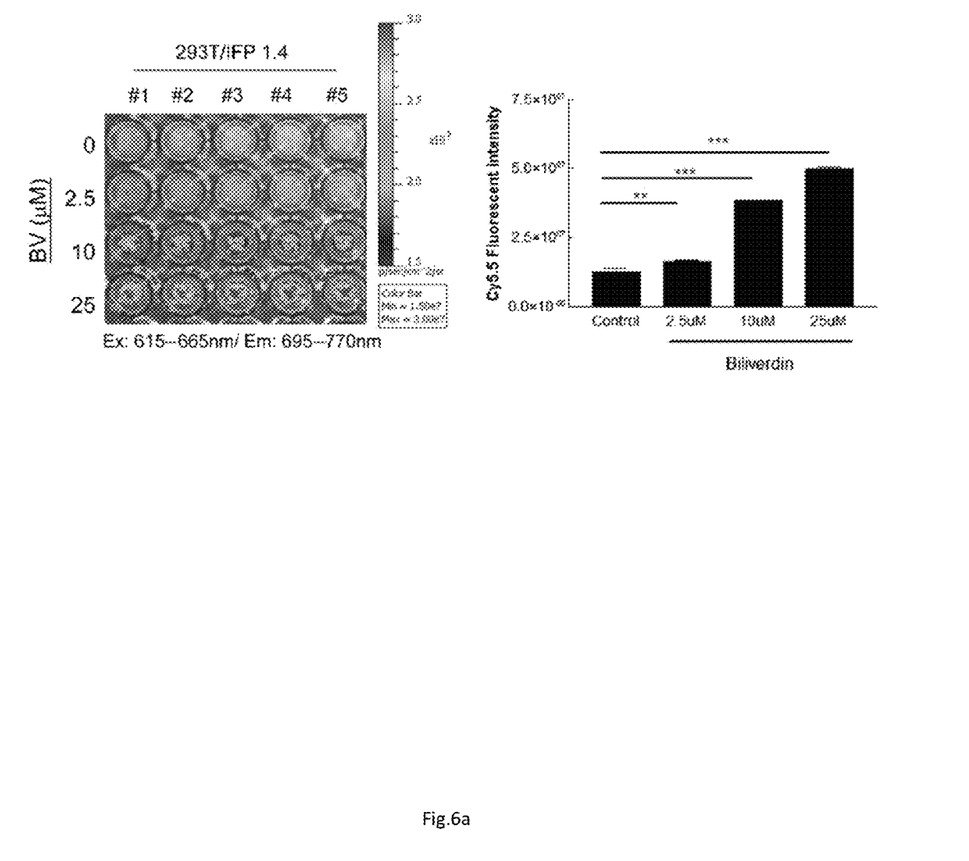
FIG. 6a illustrates the effect of BV on the fluorescent light brightness of IFP 1.4.

Next, the fluorescent imaging was used to investigate whether the expression of mPlum-IFP 1.4 fusion protein was detectable in vivo. The nude mice were subcutaneously implanted with tumorigenic 293T cells transfected with the mPlum-IFP 1.4 fusion construct, or co-transfected with the IFP 1.4 and the mPlum constructs. These mice were then subjected to the IVIS system. Referring to FIG. 6a, cells expressing the mPlum-IFP 1.4 fusion protein construct could be detected in implanted small animals when excited using the DsRed (ex: 580 to 610 nm) channel but not using the Cy5.5 (ex 615 to 665 nm) channel. Additionally, intravenous injection of the BV did not enhance the fluorescent signals of the mPlum-IFP 1.4 fusion protein. On the contrary, the fluorescent signals emitted from native IFP 1.4 was only detected using the Cy5.5 channel in the presence of the BV (FIG. 6a).

Figure 6B:
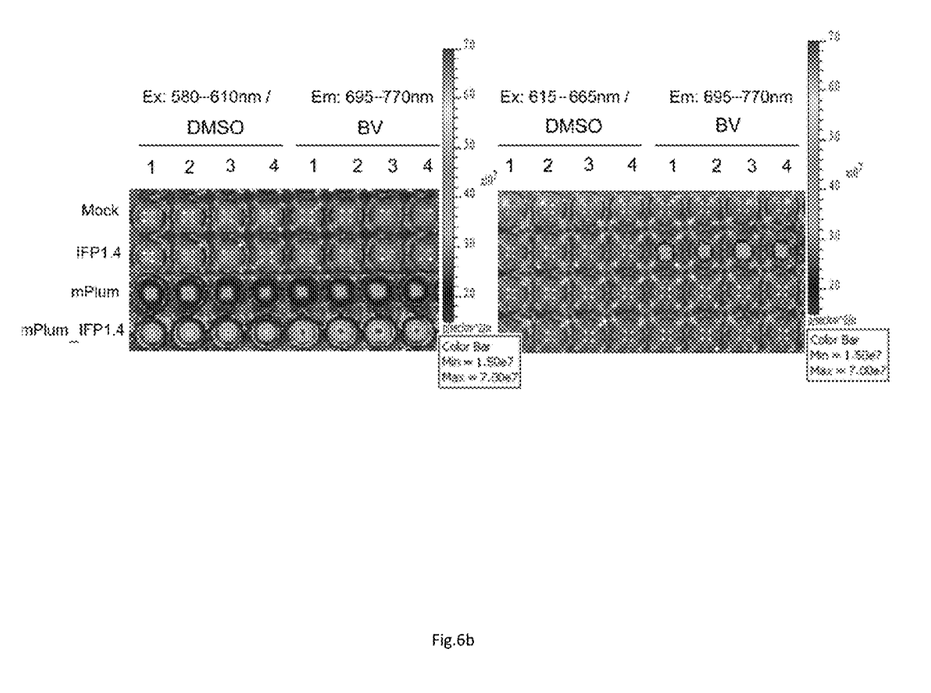
FIGS. 6b-6c illustrate the effect of BV on the fluorescent light brightness of mPlum, IFP 1.4, and mPlum-IFP 1.4 fusion protein.
Figure 6C:
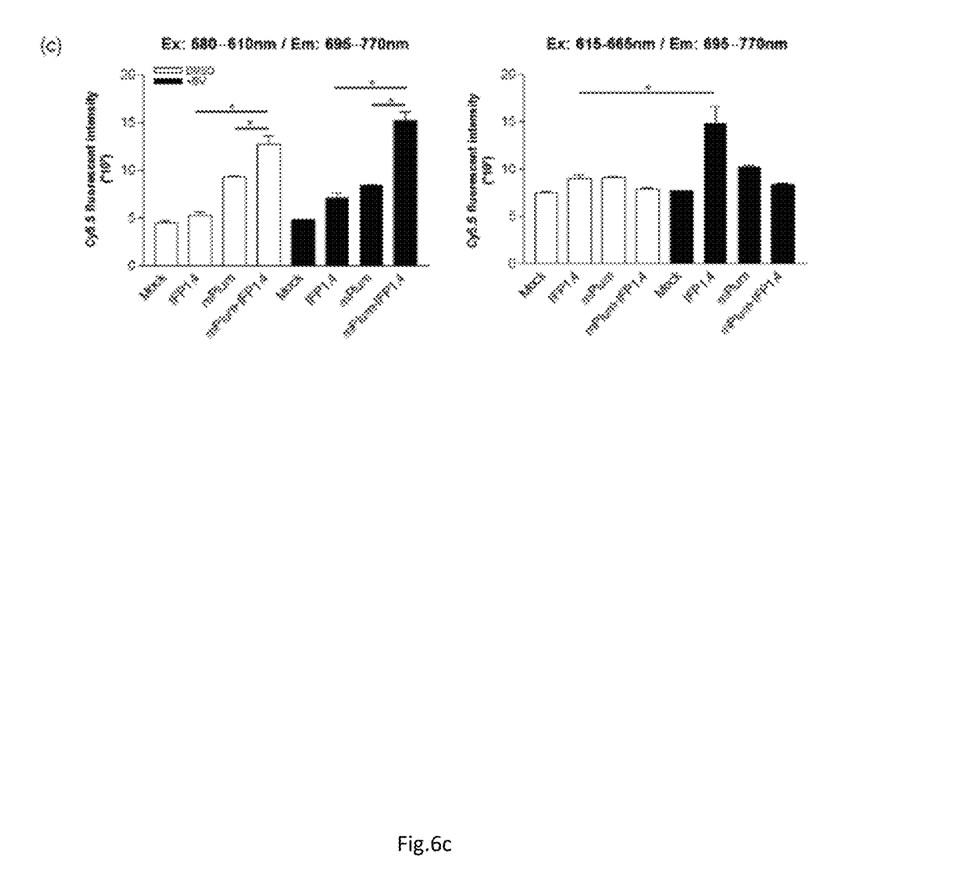
Figure 7A:
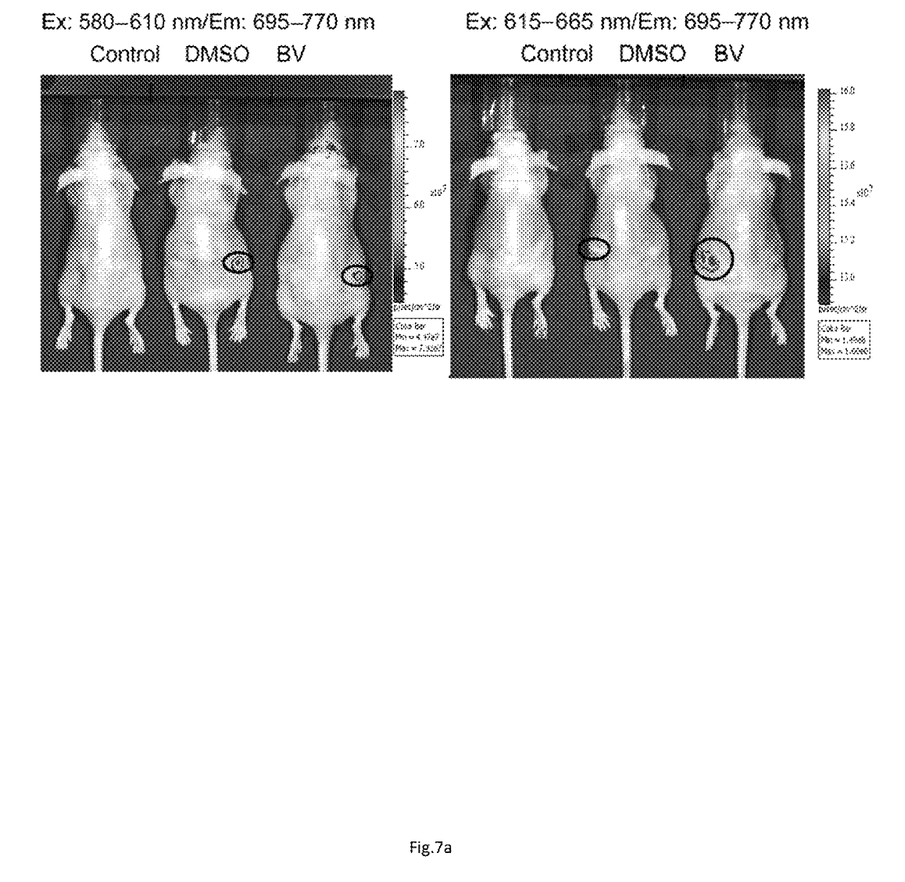
FIGS. 7a-7b illustrate the effect of BV on the fluorescent light brightness of IFP 1.4 and mPlum-IFP 1.4 fusion protein in vivo.
Figure 7B:
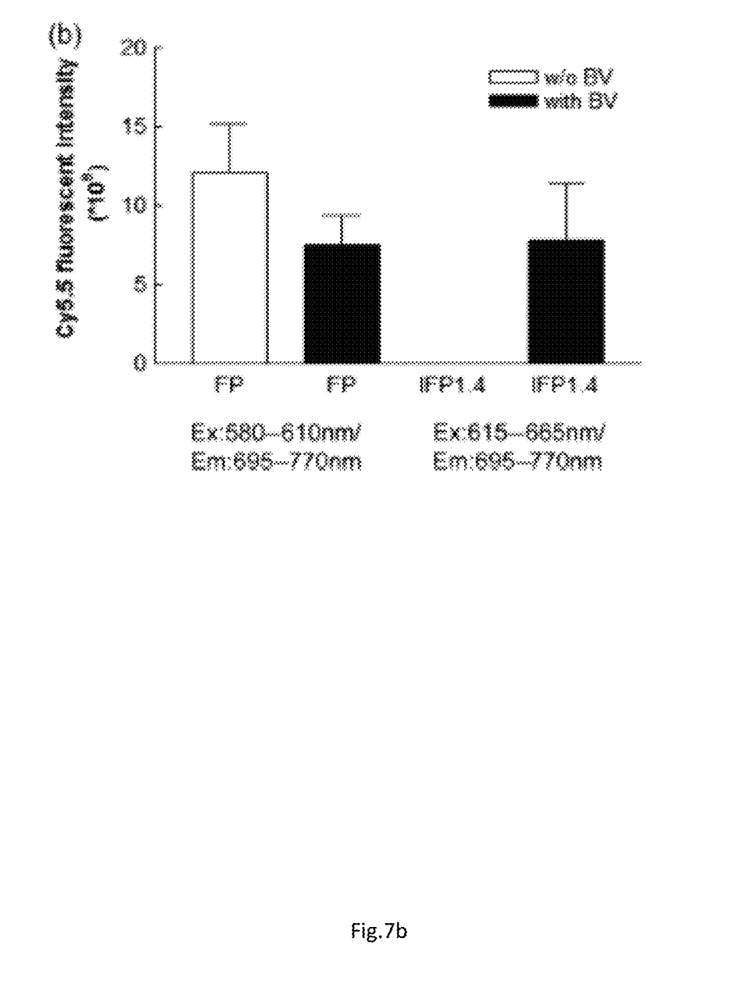

The fluorescent intensity was also semi-quantified by selected regions of interests, and no significant difference was detected in fusion proteins with or without BV injection, compared to IFP 1.4 alone (FIG. 6b). Therefore, the mPlum-IFP 1.4 fusion protein would be useful for the in vivo fluorescent imaging without an extra injection of the BV to enhance the signals.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A fluorescent fusion protein comprising
a first fluorescent protein with a first emission wavelength, wherein the first fluorescent protein is mPlum;
a linker peptide linking the C-terminal of the first fusion protein, wherein the linker peptide has a sequence of SEQ ID: NO.:1; and
a second fluorescent protein linking the C-terminal of the linker peptide, wherein the second fluorescent protein has a second excitation wavelength and a second emission wavelength, wherein the second fluorescent protein is IFP 1.4;
wherein the first emission wavelength overlaps the second excitation wavelength so that the second fluorescent protein exhibits the second emission wavelength after receiving energy.

2. The fluorescent fusion protein according to claim 1, wherein the first emission wavelength is between 600 nm and 690 nm.

3. The fluorescent fusion protein according to claim 1, wherein the second excitation wavelength is between 600 nm and 690 nm.

4. The fluorescent fusion protein according to claim 1, wherein the second emission wavelength is between 620 nm and 708 nm.

5. The fluorescent fusion protein according to claim 1, wherein the first emission wavelength overlaps the second excitation wavelength.

6. A kit comprising the fluorescent fusion protein of claim 1.

* * * * *